United States Patent
Lee et al.

(10) Patent No.: US 8,852,945 B2
(45) Date of Patent: Oct. 7, 2014

(54) METHOD FOR DETECTING SOUR ODOR FROM AIR CONDITIONER, REPRODUCING SOUR ODOR AND PREPARING CORRESPONDING SOUR ODOR COMPOSITION

(71) Applicant: Hyundai Motor Company, Seoul (KR)

(72) Inventors: Tae Hee Lee, Gyeonggi-do (KR); Ji Wan Kim, Gyeonggi-do (KR)

(73) Assignee: Hyundai Motor Company, Seoul (KR)

( * ) Notice: Subject to any disclaimer, the term of this patent is extended or adjusted under 35 U.S.C. 154(b) by 16 days.

(21) Appl. No.: 13/693,768

(22) Filed: Dec. 4, 2012

(65) Prior Publication Data
US 2014/0087475 A1   Mar. 27, 2014

(30) Foreign Application Priority Data
Sep. 25, 2012 (KR) .................. 10-2012-0106656

(51) Int. Cl.
  G01N 33/00  (2006.01)
  G01N 31/00  (2006.01)
  G01N 30/02  (2006.01)
  G01N 30/88  (2006.01)

(52) U.S. Cl.
  CPC ............ G01N 30/02 (2013.01); G01N 33/0004 (2013.01); G01N 2030/8809 (2013.01); G01N 33/0001 (2013.01)
  USPC .................. 436/9; 436/8; 436/113; 436/128; 436/140; 436/161; 436/173; 436/174; 252/408.1; 252/372; 73/23.34

(58) Field of Classification Search
  CPC ..... G01N 1/22; G01N 1/2202; G01N 1/2214; G01N 1/2247; G01N 31/00; G01N 33/00; G01N 33/0004; G01N 33/0054
  USPC ......... 436/8, 9, 106, 111, 113, 119, 120, 127, 436/128, 130, 131, 139, 140, 141, 161, 173, 436/174; 252/408.1, 372; 73/23.2, 23.34
  See application file for complete search history.

(56) References Cited

U.S. PATENT DOCUMENTS

2005/0191213 A1* 9/2005 Casillas et al. .................. 422/99

FOREIGN PATENT DOCUMENTS

| JP | 05045260 A | 2/1993 |
| JP | 2004239921 A | 8/2004 |
| KR | 10-0620060 | 8/2006 |

OTHER PUBLICATIONS

Kim et al. Journal of Chromatography A, vol. 1204, Jul. 17, 2008, pp. 72-80.*
Chung et al. Environmental Monitoring Assessment, vol. 177, Jul. 27, 2010, pp. 73-84.*
Ray et al. Chemosphere, vol. 87, Jan. 23, 2012, pp. 557-565.*
Rahman et al. Journal of Hazardous Materials, vol. 215-216, Mar. 3, 2012, pp. 233-242.*
Lee, Tae-woong. "Evaluation of VOC and odor on car air conditioning evaporator with an without coating", Dept. of Environ. Sci. Grad. school, Kangwon National University, 70 pages, 2010.

* cited by examiner

*Primary Examiner* — Maureen Wallenhorst
(74) *Attorney, Agent, or Firm* — Edwards Wildman Palmer LLP; Peter F. Corless

(57) ABSTRACT

Disclosed herein is a method for identifying compounds contributing to a sour odor emitting from an air conditioner, a method for artificially reproducing the detected sour odor and preparing a corresponding sour odor composition. Through the analysis method of the present invention, the compounds contributing to the sour odor emitted from an air conditioner may be identified and quantified. The detected sour odor may be reproduced from a combination of the compounds identified by the analysis method of the present invention. The reproduced sour odor may provide meaningful data required for development of an apparatus and a method for removing specific odors.

7 Claims, 1 Drawing Sheet

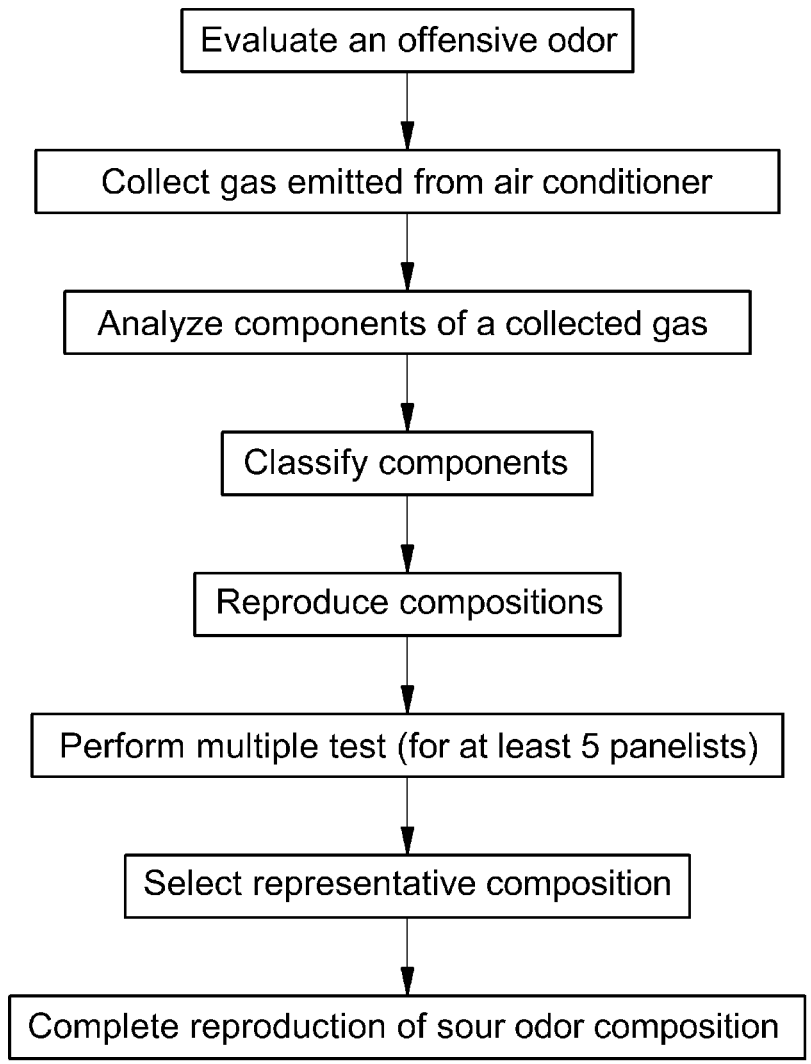

METHOD FOR DETECTING SOUR ODOR FROM AIR CONDITIONER, REPRODUCING SOUR ODOR AND PREPARING CORRESPONDING SOUR ODOR COMPOSITION

CROSS-REFERENCE

This application claims priority under 35 U.S.C. §119 to Korean Patent Application No. 10-2012-0106656, filed on Sep. 25, 2012, the disclosure of which is incorporated herein in its entirety by reference.

BACKGROUND OF THE INVENTION

1. Field of the Invention

The present invention relates to a method for detecting a combination of compounds contributing to sour odor from an air conditioner, a method for reproducing the sour odor and preparing a corresponding sour odor composition.

2. Description of the Related Art

Clean air is an essential element to help humans stay in good health and maintain their well-beings. Two important factors that lead to unsatisfactory indoor air quality in an airtight building are: the building itself producing a substantial amount of air pollutants that need to be removed or diluted; and odor generated as a result of human activities.

An air-cooling system lowers indoor temperature and optimizes indoor environment through air conditioning, which changes air temperature, humidity, flow and cleanliness to more favorable conditions. Increasingly, air-cooling systems are being used to improve the standard of living. Although the air-cooling systems have been improved functionally over time, there remain problems to be solved in terms of indoor air quality. In the past, the function of lowering indoor temperature was viewed as one of the most fundamental and important functions of the air-cooling system. However, currently, health-related aspects such as indoor air quality and odor are also regarded as important functions of air-cooling systems. In particular, complaints regarding indoor air quality include offensive odor such as sour odor, foul odor, foot odor, and the like. To solve the odor problem, it may be necessary to analyze the odor-causing substances and understand the fundamental cause of the odor.

Although it is known that metabolites produced by fungi and bacteria are the cause of odor from an air conditioner, it is clearly not known what metabolites are produced and in what amount by the fungi and bacteria. Additionally, since it is unclear specifically what compounds cause the offensive odor, it may be necessary to understand the type of compounds which contribute to the sour odor from the air conditioner.

SUMMARY OF THE INVENTION

Numerous complaints are commonly made regarding various offensive odors from an air conditioner (e.g., more than 20 kinds including musty odor). The present invention discloses a method for identifying the compounds contributing to the sour odor emitted from an air conditioner, collecting offensive-smelling gas from an automobile, and developing a method for artificially reproducing the sour odor. The present invention provides a method for detecting the compounds contributing to sour odor from an air conditioner from among various offensive odors emitted from the air conditioner.

The present invention also discloses a method for identifying the compounds contributing to sour odor from emitted an air conditioner from among various offensive odors emitted from the air conditioner and artificially reproducing the sour odor using the identified chemical compounds. Additionally, the present invention discloses a method of preparing a sour odor composition. The sour odor composition may also be applicable to any applications where sour odor is emitted, in addition to the air conditioner.

In one embodiment, the present invention provides a sour odor composition from an air conditioner comprising one or more compounds selected from a group consisting of ammonia, acetaldehyde, propionaldehyde, n-butyraldehyde, toluene, xylene and methyl ethyl ketone.

In another embodiment, the present invention provides a sour odor composition from an air conditioner comprising ammonia, acetaldehyde, propionaldehyde, n-butyraldehyde, toluene, xylene and methyl ethyl ketone.

In yet another embodiment, the present invention provides a method for analyzing the compounds contributing to sour odor from an air conditioner, including the steps of (i) collecting a gas emitted from an air conditioner; and (ii) analyzing the components of the gas.

In another aspect, the present invention provides a method for preparing a sour odor composition from an air conditioner, comprising mixing two or more compounds selected from a group consisting of ammonia, acetaldehyde, propionaldehyde, n-butyraldehyde, toluene, xylene and methyl ethyl ketone.

Other features and aspects of the present invention will be apparent from the following detailed description and the accompanying drawings and claims.

BRIEF DESCRIPTION OF THE DRAWING

The above and other objects, features and advantages of the present invention will now be more clearly understood from the following detailed description taken in conjunction with the accompanying drawing which are given hereinbelow by way of illustration only, and thus are not limitative of the invention, and wherein:

FIG. 1 is an exemplary flow chart describing a method for analyzing the compounds contributing to sour odor according to an exemplary embodiment of the present invention.

DESCRIPTION OF THE PREFERRED EMBODIMENTS

Hereinafter, reference will be made in detail to various embodiments of the present invention, examples of which are illustrated in the accompanying drawings and described below. While the invention will be described in conjunction with exemplary embodiments, it will be understood that the present description is not intended to limit the invention to those exemplary embodiments. On the contrary, the invention is intended to cover not only the exemplary embodiments, but also various alternatives, modifications, equivalents and other embodiments, which may be included within the spirit and scope of the invention as defined by the accompanying claims.

In one embodiment, the present invention provides a detected sour composition from an air conditioner having at least one or more of the following compounds: ammonia, acetaldehyde, propionaldehyde, n-butyraldehyde, toluene, xylene and methyl ethyl ketone.

More specifically, the present invention provides a detected sour odor composition from an air conditioner including ammonia, acetaldehyde, propionaldehyde, n-butyraldehyde, toluene, xylene and methyl ethyl ketone.

The sour odor composition from an air conditioner may include:

0.1-2 ppm of ammonia;
0.002-0.1 ppm of acetaldehyde;
0.0001-0.1 ppm of propionaldehyde;
0.0003-0.03 ppm of n-butyraldehyde;
0.03-30 ppm of toluene;
0.001-2 ppm of xylene; and
0.003-7 ppm of methyl ethyl ketone.

In an exemplary embodiment of the present invention, the detected sour odor composition may further comprise one or more compound selected from a group consisting of formaldehyde, hexane, N-phenylbenzenamine, phenol, 2-phenyl-2propanol, benzene and benzothiazole.

Specifically, the sour odor composition may include:

0.00002-0.009 ppm of formaldehyde;
0.007-0.04 ppm of hexane;
0.001-0.4 ppm of N-phenylbenzenamine;
0.003-0.6 ppm of phenol;
0.001-0.2 ppm of 2-phenyl-2propanol;
0.001-0.2 ppm of benzene; and
0.001-0.1 ppm of benzothiazole.

In another embodiment, the present invention provides a method for analyzing the compounds contributing to sour odor from an air conditioner. The method includes the steps of (i) collecting a gas emitted from an air conditioner and (ii) analyzing the components of the gas.

In another aspect, the present invention provides a method for analyzing the compounds contributing to sour odor from an air conditioner and reproducing the sour odor. The method includes the steps of: evaluating offensive odor; collecting a gas emitted from an air conditioner; analyzing the components of the collected gas; classifying the components; reproducing compositions; performing a multiple test (e.g., for at least 5 panelists); selecting the representative composition; and completing the reproduction of the sour odor composition.

FIG. 1 is an exemplary flow chart describing the method for analyzing the compounds contributing to sour odor and reproducing the sour odor.

The sour odor from an air conditioner of the present invention may be from an air conditioner in any environment including building, automobile, van, bus, etc. More specifically, the air conditioner may be an air conditioner used in an automobile, van or bus.

In an exemplary embodiment of the present invention, the gas in step (ii) may comprise ammonia, acetaldehyde, propionaldehyde, n-butyraldehyde, toluene, xylene and methyl ethyl ketone. The concentration of the ammonia, acetaldehyde, propionaldehyde, n-butyraldehyde, toluene, xylene and methyl ethyl ketone that contribute to the sour odor may be measured. Additionally, the concentration of one or more compound selected from a group consisting of formaldehyde, hexane, N-phenylbenzenamine, phenol, 2-phenyl-2propanol, benzene and benzothiazole in the sour odor composition may be measured. The analysis of the components in step (ii) may be performed by gas chromatography/mass spectrometry (GC/MS), gas chromatography with atomic emission detector (GC/AED), gas chromatography/flame ionization detection/olfactometry (GC/FID/olfactometry) or high-performance liquid chromatography (HPLC), but is not limited thereto.

Representative examples of the analysis method of the present invention are described hereinbelow. However, the analysis method of the present invention is not limited thereto.

Gas Chromatography

In gas-solid chromatography (GSC), an adsorbent solid powder may be used as the stationary phase. In addition, in gas-liquid chromatography (GLC), a liquid stationary phase coated on a solid support may be used.

A carrier gas maintained at a constant flow rate may be supplied from a sample injection device into a separation column via a pretreatment apparatus and may be discharged after passing through a detector. The pretreatment apparatus, the sample injection device, the column and the detector may be maintained at required temperatures.

When a gas or a liquid is introduced into the sample injection device, the gas may be carried into the column by the carrier gas and the liquid may be carried into the column by the carrier gas after being heated and evaporated. The components of the sample may be separated in the separation column based on difference in absorption or solubility and may sequentially pass through a mass analyzer disposed at the outlet of the separation column.

The time between the injection of the sample into the separation column and a peak occurrence, as a result of detection of a specific component included therein, may be called retention time. Additionally, the retention time multiplied by the flow rate of the carrier gas may be called retention volume. Qualitative analysis may be performed on the process since the values of the retention time and volume may be different for different components under given experimental conditions. Furthermore, quantitative analysis may be conducted since the peak area or height may be related to the amount of the corresponding component present.

Electron ionization is a conventionally used ionization technique. Neutral sample molecules in gas state are bombarded with high-speed electrons to detach electrons and form molecular ions (cations, $M^+$). The minimum energy required to produce the molecular ion (M+) from the neutral molecule (M) is called ionization energy (IE). The ionization energy of an organic compound is 8-12 eV (800-1200 kJ/mol$^{-1}$).

$$M + e^- \rightarrow M^+ + 2e^-$$

Among the produced molecular ions, those with high internal energy are fragmented to form fragment ions.

To prevent ion formation due to reaction between the produced ion and the neutral molecule, the pressure inside the ionization source should be maintained at $10^{-5}$ torr or lower.

Electron beams emitted from a filament may be accelerated to 70 eV to obtain standard mass spectrums since they provide high ionization efficiency with little change in mass spectrum. The mass spectrum is the recording of the mass-to-charge ratio (m/z) of the molecular ions and the fragment ions. The mass spectrum of the unknown sample may be compared with the stored standard mass spectrums to identify the substance.

Electric fields and magnetic fields may be utilized alone or in combination to separate the ions according to their mass-to-charge ratio. A sector field analyzer, a quadruple mass analyzer, an ion trap, a time-of-flight analyzer, and the like may be used as a mass analyzer.

High-Performance Liquid Chromatography (HPLC)

The HPLC method may be utilized to separate nonvolatile substances which may be difficult to analyze by gas chromatography based on their difference in physicochemical interactions with a stationary phase and a liquid mobile phase. This method may be used for qualitative and quantitative analysis of aldehydes in the air. Additionally, in HPLC, the target substances may be separated in the separation column based on their difference in reactivity with the stationary phase and the mobile phase.

When HPLC is employed for analysis of aldehydes existing in the air, a separation column in which a nonpolar stationary phase is chemically bonded to a support may be used. Separation may be achieved depending on difference in reactivity and solubility for the mobile phase and the stationary phase. In general, the method wherein a column containing a nonpolar stationary phase is used and a relatively polar sample eluent is used to separate target substances is called reversed-phase HPLC.

The material of the tubing in the HPLC method may be stainless steel, PTFE, PEEK, glass, or a similar material. Generally, stainless steel may be preferable. Stainless steel may be advantageous due to being resistant to oxidation and corrosion. However, acid may cause damage and contamination to the tubing. Thus, when stainless steel is used, the tubing should be washed with distilled water after use.

Most often, an HPLC detector capable of measuring absorption in the UV-visible region may be used. When light of a particular wavelength is emitted from a light source on the sample in the cell of the UV-visible detector, it may be absorbed by the sample. The detector may generate an electrical signal corresponding to the light absorbance, thus allowing quantitative analysis of the sample.

Hereinafter, the method for detecting the components contributing to sour odor according to the present invention is described. However, the application of the method is not limited to the described components.

Detection of Ammonia

The concentration of ammonia in the air may be measured as follows. After adding a phenol-sodium nitroprusside solution and a sodium hypochlorite solution to a sample solution to be analyzed, ammonia may be analyzed by measuring absorbance of indophenols formed from reaction with ammonium ion.

Detection of Methyl Mercaptan, Hydrogen Sulfide, Dimethyl Sulfide and Dimethyl Disulfide The concentration of the sulfur compounds in the air may be measured as follows.

After sampling using a sample bag, analysis may be carried out by cold trap-capillary GC and cold trap-packed column GC.

Cold Trap-Capillary GC and Cold Trap-Packed Column GC

The sulfur compound sample collected in the sample bag may be concentrated in a cold trap device, which may be maintained at $-183°$ C. or below using a refrigerant and may be analyzed by GC after desorption. The measurement procedure may consist of sampling, concentration and sample injection to the separation column. A flame photometric detector (FPD), a pulsed flame photometric detector (PFPD), an atomic emission detector (AED), a sulfur chemiluminescence detector (SCD), a mass spectrometer (MS), and the like capable of selectively detecting trace amount of sulfur compounds with good linearity may be used as a detector.

Electronic Device Cooling Cold Trap-Capillary GC

Sulfur compounds existing in the sample may be concentrated at low temperature using a cold trap, desorbed at moderate temperature, and transferred into a syringe pump by the pressure of a carrier gas. The desorption may occur at moderate-to-low temperatures (e.g., $100°$ C. or lower). The concentrated sample transferred to the syringe pump may be injected into the separation column and analyzed by the detector. The cold-trapped sample may also be thermally desorbed and injected into the separation column.

Detection of Triethylamine

The concentration of triethylamine in the air may be measured as follows. After sampling using an impinger and acidic filter paper, analysis may be carried out by cold trap-packed column GC and headspace-capillary column GC.

Detection of Acetaldehyde, Propionaldehyde, Butyraldehyde, n-Valeraldehyde and Isovaleraldehyde For simultaneous measurement of the concentration of acetaldehyde, propionaldehyde, butyraldehyde, n-valeraldehyde and isovaleraldehyde contributing to offensive odor, 2,4-dinitrophenylhydrazone (DNPH) derivatives of the aldehyde compounds may be formed and analyzed by HPLC and GC.

Dinitrophenylhydrazine (DNPH) Derivatization and HPLC/UV

DNPH derivatives formed by reacting carbonyl compounds with 2,4-DNPH may be extracted with an acetonitrile solvent and analyzed by HPLC using a UV detector at 360 nm wavelength.

DNPH Derivatization and GC

DNPH derivatives formed by reacting carbonyl compounds with 2,4-DNPH may be extracted with an acetonitrile solvent and analyzed by GC after changing the solvent to ethyl acetate.

HPLC Instrument

The HPLC instrument for sample analysis may consist of a sample injection device, a pump, a separation column and a detector (UV detector). The separation column may be a reversed-phase column (ODS column) to which a nonpolar adsorbent is coated allowing control of the mobile phase solvent according to the mixing ratio. The sample loop of the injection device may be 20-100 mL depending on the sample concentration.

GC Instruments

A capillary separation column may be used for GC, and a flame ionization detector (FID), a nitrogen phosphorus detector (NPD) or a mass spectrometer may be used as the detector.

Detection of Styrene

Styrene may be sampled at the site boundary. After sampling, using a solid sorbent tube, a canister or a sample bag, analysis may be carried out by cold trap-GC and solid-phase microextraction (SPME)-GC.

Detection of Toluene, Xylene, Methyl Ethyl Ketone, Methyl Isobutyl Ketone, Butyl Acetate, Styrene and Isobutyl Alcohol The concentration of toluene, xylene, methyl ethyl ketone, methyl isobutyl ketone, butyl acetate, styrene and isobutyl alcohol, which are volatile compounds contributing to offensive odors, in the air may be measured at once as follows.

Toluene, xylene, methyl ethyl ketone, methyl isobutyl ketone, butyl acetate, styrene and isobutyl alcohol may be specified offensive odor substances. Sampling may be performed at the site boundary. The sample collected using a solid sorbent tube may be analyzed by GC after cold trapping and thermal desorption.

Detection of Propionic Acid, n-Butyric Acid, n-Valeric Acid and Isovaleric Acid

The concentration of the organic acids in the air may be measured as follows. After sampling using an alkaline-impregnated filter or by alkaline solution absorption, the collected sample may be pretreated by the headspace method to evaporate the organic acid components. Then, analysis may be carried out by GC.

In another embodiment, the present invention provides a method for preparing a sour odor composition from an air conditioner, including mixing two or more compounds selected from a group consisting of ammonia, acetaldehyde, propionaldehyde, n-butyraldehyde, toluene, xylene and methyl ethyl ketone.

In another embodiment, the present invention provides a method for preparing a sour odor composition from an air conditioner, including mixing ammonia, acetaldehyde, propionaldehyde, n-butyraldehyde, toluene, xylene and methyl ethyl ketone.

In yet another exemplary embodiment of the present invention, the method for preparing a sour odor composition from an air conditioner may include mixing one or more compound selected from a group consisting of formaldehyde, hexane, N-phenylbenzenamine, phenol, 2-phenyl-2propanol, benzene and benzothiazole.

In an exemplary embodiment of the present invention, the method for preparing a sour odor composition from an air conditioner according to the present invention may include mixing: 0.1-2 ppm of ammonia; 0.002-0.1 ppm of acetaldehyde; 0.0001-0.1 ppm of propionaldehyde; 0.0003-0.03 ppm of n-butyraldehyde; 0.03-30 ppm of toluene; 0.001-2 ppm of xylene; and 0.003-7 ppm of methyl ethyl ketone.

In another exemplary embodiment of the present invention, the method for preparing a sour odor composition from an air conditioner according to the present invention may include mixing: 0.00002-0.009 ppm of formaldehyde; 0.007-0.04 ppm of hexane; 0.001-0.4 ppm of N-phenylbenzenamine; 0.003-0.6 ppm of phenol; 0.001-0.2 ppm of 2-phenyl-2propanol; 0.001-0.2 ppm of benzene; and 0.001-0.1 ppm of benzothiazole.

EXAMPLES

The present invention will be described in more detail through examples. The following examples are for illustrative purposes only and it will be apparent to those skilled in the art not that the scope of this invention is not limited by the examples.

Example 1

Sensory Test

1) Selection of Car Model
Odor was sampled from the air conditioner of a car model A.
2) Sensory Test Method
i) Three out of the four air conditioner exhausts were sealed hermetically.
ii) For sensory test and gas sampling, the exhaust at the left side of the driver's seat was sealed hermetically using a glass tube and a vinyl bag.
iii) The air conditioner was operated at level 2 under internal ventilation condition.
iv) The panelist was asked to sniff the sample in the glass tube and evaluate the intensity and type of odor.

Table 1 describes the level of odor according to intensity used as the standard of sensory test and evaluation after preparation of the mixtures for reproducing the odor in Examples 3 and 4.

TABLE 1

| Odor intensity | Level of odor |
| --- | --- |
| 5 | Irritating and intense odor |
| 4 | Strong odor |
| 3 | Weak but easily perceived odor |
| 2 | Perceived but slight odor |
| 1 | Almost unperceived odor |
| 0 | No odor |

Example 2

Sampling Procedure

1) Selection of Car Model
Sample was taken from the same car as in Example 1.
2) Sampling Method
i) Three out of the four air conditioner exhausts were sealed hermetically.
ii) The exhaust at the left side of the driver's seat was sealed hermetically using a glass tube and a vinyl bag.
iii) The opening of a 10-L PE sample bag was connected to the glass tube.
iv) The air conditioner was operated at level 2 under internal ventilation condition and gas sample was taken.

Example 3

Sample Analysis

The sample taken in Example 2 was analyzed by absorption spectrophotometry, HS-GC/FID, GC/FPD, HPLC/UV, GC/MSD and HS-GC/MS.

Table 2 shows the result of detecting representative compounds contributing to offensive odor.

TABLE 2

| | | Car model #1 | Car model #2 | Car model #3 | Car model #4 | Car model #5 |
| --- | --- | --- | --- | --- | --- | --- |
| Sensory test | Characteristic | Sour odor | Leather/sour odor | Sour/plastic odor | Sour/plastic odor | Sour odor |
| | Intensity | 2-3 | 2-3 | 2-3 | 2-3 | 3-4 |
| Analysis of specified offensive odor substances (unit: ppm) | Ammonia | 0.10 | 0.03 | 0.06 | 0.03 | 0.03 |
| | Dimethyl disulfide | ND | 0.00003 | ND | ND | ND |
| | Acetaldehyde | 0.00686 | 0.00412 | 0.00548 | 0.00471 | 0.00380 |
| | Styrene | ND | ND | 0.00588 | ND | ND |
| | Propionaldehyde | 0.00017 | 0.00025 | 0.00022 | 0.00034 | 0.00020 |
| | n-Butyraldehyde | 0.00045 | 0.02650 | 0.00702 | 0.02344 | 0.00053 |
| | Toluene | 0.05865 | 0.03492 | 0.04006 | 0.04931 | 0.05194 |
| | Xylene | 0.00151 | 0.00116 | 0.00110 | 0.00144 | 0.00143 |
| | Methyl ethyl ketone | 0.00945 | 0.01780 | 0.00364 | 0.02229 | 0.02611 |

TABLE 2-continued

|  | Car model #1 | Car model #2 | Car model #3 | Car model #4 | Car model #5 |
|---|---|---|---|---|---|
| Methyl ethyl ketone | 0.00945 | 0.01780 | 0.00364 | 0.02229 | 0.02611 |

10-mL samples were taken from the car models #1-#5 under the condition of blower level 2+air conditioner off-on-off.

Example 4

Preparation of Sour Odor Composition

A sour odor composition was prepared by mixing ammonia, acetaldehyde, propionaldehyde, n-butyraldehyde, toluene, xylene and methyl ethyl ketone among the components described in Table 2 and further mixing the additional components described in Table 3 (car model #1), Table 4 (car model #2), Table 5 (car model #3), Table 6 (car model #4) and Table 7 (car model #5).

TABLE 3

|  | Final concentration (ppm) | Final volume (L) | Temperature (°C.) | Pressure (mb) | Mass (μg) |
|---|---|---|---|---|---|
| Ammonia | 0.1 | 10 | 20 | 1013.25 | 0.000708394 |
| Acetaldehyde | 0.00686 | 10 | 20 | 1013.25 | 0.000125649 |
| Propionaldehyde | 0.00017 | 10 | 20 | 1013.25 | 4.17946E−06 |
| n-Butyraldehyde | 0.00045 | 10 | 20 | 1013.25 | 1.3527E−05 |
| Toluene | 0.05865 | 10 | 20 | 1013.25 | 0.00224765 |
| Xylene | 0.00151 | 10 | 20 | 1013.25 | 6.67713E−05 |
| Methyl ethyl ketone | 0.00945 | 10 | 20 | 1013.25 | 0.000283406 |
| Additional components | | | | | |
| Benzothiazole | 0.01315 | 10 | 20 | 1013.25 | 0.000739483 |
| N-phenylbenzenamine | 0.03346 | 10 | 20 | 1013.25 | 0.002355342 |
| Phenol | 0.04813 | 10 | 20 | 1013.25 | 0.001884198 |
| 2-Phenyl-2-propanol | 0.01602 | 10 | 20 | 1013.25 | 0.000907384 |
| Benzene | 0.01478 | 10 | 20 | 1013.25 | 0.000480289 |
| Hexane | 0.07896 | 10 | 20 | 1013.25 | 0.028775467 |
| Trimethylsilanol | 0.00678 | 10 | 20 | 1013.25 | 0.000254502 |
| Formaldehyde | 0.00050 | 10 | 20 | 1013.25 | 6.28305E−06 |

TABLE 4

|  | Final concentration (ppm) | Final volume (L) | Temperature (°C.) | Pressure (mb) | Mass (μg) |
|---|---|---|---|---|---|
| Ammonia | 0.03 | 10 | 20 | 1013.25 | 0.000212518 |
| Dimethyl disulfide | 0.00003 | 10 | 20 | 1013.25 | 1.29306E−06 |
| Acetaldehyde | 0.00412 | 10 | 20 | 1013.25 | 7.54589E−05 |
| Propionaldehyde | 0.00025 | 10 | 20 | 1013.25 | 5.94305E−06 |
| n-Butyraldehyde | 0.02650 | 10 | 20 | 1013.25 | 0.000794792 |
| Toluene | 0.03492 | 10 | 20 | 1013.25 | 0.001338242 |
| Xylene | 0.00116 | 10 | 20 | 1013.25 | 5.10059E−05 |
| Methyl ethyl ketone | 0.01780 | 10 | 20 | 1013.25 | 0.000534 |
| Additional components | | | | | |
| Benzothiazole | 0.01439 | 10 | 20 | 1013.25 | 0.000809206 |
| N-phenylbenzenamine | 0.01538 | 10 | 20 | 1013.25 | 0.00108256 |
| Phenol | 0.03106 | 10 | 20 | 1013.25 | 0.001215752 |
| 2-Phenyl-2-propanol | 0.01323 | 10 | 20 | 1013.25 | 0.000749258 |
| Benzene | 0.01364 | 10 | 20 | 1013.25 | 0.000443212 |
| 2-Pinene | 0.01343 | 10 | 20 | 1013.25 | 0.000760958 |
| Hexane | 0.07180 | 10 | 20 | 1013.25 | 0.026167709 |
| Trimethylsilanol | 0.00356 | 10 | 20 | 1013.25 | 0.000133399 |
| Formaldehyde | 0.00085 | 10 | 20 | 1013.25 | 1.06674E−05 |

TABLE 5

| | Final concentration (ppm) | Final volume (L) | Temperature (° C.) | Pressure (mb) | Mass (μg) |
|---|---|---|---|---|---|
| Ammonia | 0.06 | 10 | 20 | 1013.25 | 0.000425036 |
| Acetaldehyde | 0.00548 | 10 | 20 | 1013.25 | 0.000100398 |
| Styrene | 0.00588 | 10 | 20 | 1013.25 | 0.000254779 |
| Propionaldehyde | 0.00022 | 10 | 20 | 1013.25 | 5.29076E−06 |
| n-Butyraldehyde | 0.00702 | 10 | 20 | 1013.25 | 0.000210553 |
| Toluene | 0.04006 | 10 | 20 | 1013.25 | 0.001535163 |
| Xylene | 0.00110 | 10 | 20 | 1013.25 | 4.85329E−05 |
| Methyl ethyl ketone | 0.00364 | 10 | 20 | 1013.25 | 0.000109026 |
| Additional components | | | | | |
| Benzothiazole | 0.01353 | 10 | 20 | 1013.25 | 0.000760555 |
| N-phenylbenzenamine | 0.04373 | 10 | 20 | 1013.25 | 0.003078221 |
| Phenol | 0.06221 | 10 | 20 | 1013.25 | 0.002435121 |
| 2-Phenyl-2-propanol | 0.02080 | 10 | 20 | 1013.25 | 0.001178031 |
| Benzene | 0.02348 | 10 | 20 | 1013.25 | 0.00076281 |
| Ethylbenzene | 0.00301 | 10 | 20 | 1013.25 | 0.000132948 |
| Hexane | 0.06942 | 10 | 20 | 1013.25 | 0.025300046 |
| N,N-dimethylacetamide | 0.05830 | 10 | 20 | 1013.25 | 0.002112775 |
| Trimethylsilanol | 0.00396 | 10 | 20 | 1013.25 | 0.000148461 |
| Formaldehyde | 0.00083 | 10 | 20 | 1013.25 | 1.04051E−05 |

TABLE 6

| | Final concentration (ppm) | Final volume (L) | Temperature (° C.) | Pressure (mb) | Mass (μg) |
|---|---|---|---|---|---|
| Ammonia | 0.03 | 10 | 20 | 1013.25 | 0.000212518 |
| Acetaldehyde | 0.00471 | 10 | 20 | 1013.25 | 8.63434E−05 |
| Propionaldehyde | 0.00034 | 10 | 20 | 1013.25 | 8.28644E−06 |
| n-Butyraldehyde | 0.02344 | 10 | 20 | 1013.25 | 0.000703042 |
| Toluene | 0.04931 | 10 | 20 | 1013.25 | 0.00188995 |
| Xylene | 0.00144 | 10 | 20 | 1013.25 | 6.37684E−05 |
| Methyl ethyl ketone | 0.02229 | 10 | 20 | 1013.25 | 0.00066864 |
| Additional components | | | | | |
| Benzothiazole | 0.01319 | 10 | 20 | 1013.25 | 0.000741522 |
| N-phenylbenzenamine | 0.02229 | 10 | 20 | 1013.25 | 0.001568783 |
| Phenol | 0.02727 | 10 | 20 | 1013.25 | 0.001067546 |
| 2-Phenyl-2-propanol | 0.01482 | 10 | 20 | 1013.25 | 0.000839426 |
| Benzene | 0.01504 | 10 | 20 | 1013.25 | 0.000488672 |
| Hexane | 0.07545 | 10 | 20 | 1013.25 | 0.027498916 |
| Formaldehyde | 0.00087 | 10 | 20 | 1013.25 | 1.08423E−05 |

TABLE 7

| | Final concentration (ppm) | Final volume (L) | Temperature (° C.) | Pressure (mb) | Mass (μg) |
|---|---|---|---|---|---|
| Ammonia | 0.03 | 10 | 20 | 1013.25 | 0.000212518 |
| Acetaldehyde | 0.00380 | 10 | 20 | 1013.25 | 6.96868E−05 |
| Propionaldehyde | 0.00020 | 10 | 20 | 1013.25 | 4.80759E−06 |
| n-Butyraldehyde | 0.00053 | 10 | 20 | 1013.25 | 1.59864E−05 |
| Toluene | 0.05194 | 10 | 20 | 1013.25 | 0.001990518 |
| Xylene | 0.00143 | 10 | 20 | 1013.25 | 6.29735E−05 |
| Methyl ethyl ketone | 0.02611 | 10 | 20 | 1013.25 | 0.000783215 |
| Additional components | | | | | |
| Benzothiazole | 0.01205 | 10 | 20 | 1013.25 | 0.000677624 |
| N-phenylbenzenamine | 0.01476 | 10 | 20 | 1013.25 | 0.001039212 |
| Phenol | 0.03338 | 10 | 20 | 1013.25 | 0.001306487 |
| 2-Phenyl-2-propanol | 0.01337 | 10 | 20 | 1013.25 | 0.000757335 |
| Benzene | 0.01096 | 10 | 20 | 1013.25 | 0.000356097 |
| Hexane | 0.09006 | 10 | 20 | 1013.25 | 0.032821056 |
| Trimethylsilanol | 0.06273 | 10 | 20 | 1013.25 | 0.002353515 |
| Formaldehyde | 0.00028 | 10 | 20 | 1013.25 | 3.46005E−06 |

The odor of the samples obtained from the air conditioner of the car models #1, #2, #3, #4 and #5 was sour odor, as described in Table 8.

The odor of the sour odor composition prepared from a combination of the aforementioned components was also sour odor of intensity 2-4, similar to that from the air conditioner.

TABLE 8

| | | Car model #1 | Car model #2 | Car model #3 | Car model #4 | Car model #5 |
|---|---|---|---|---|---|---|
| Odor from car air conditioner | Intensity | 2-3 | 2-3 | 2-3 | 2-3 | 3-4 |
| | Characteristic | Sour odor | Leather/sour odor | Sour/plastic odor | Sour/plastic odor | Sour odor |
| Sour odor composition prepared from detected compounds | Intensity | 1-2 | 2-3 | 1-2 | 1-2 | 2-3 |
| | Characteristic | Sour odor | Sour odor | Sour/plastic odor | Sour/plastic odor | Sour odor |
| Note | Intensity | Different | Similar | Different | Different | Different |
| | Characteristic | Similar | Similar | Similar | Similar | Similar |

The features and advantages of the present disclosure may be summarized as follows.

(i) Through the analysis method of the present invention, the compounds contributing to the sour odor from an air conditioner may be identified and quantified.

(ii) The sour odor may be reproduced from a combination of the compounds identified by the analysis method of the present invention.

(iii) The reproduced sour odor may provide meaningful data required for development of an apparatus and a method for removing specific odor.

The present invention has been described in detail with reference to specific embodiments thereof. However, it will be appreciated by those skilled in the art that various changes and modifications may be made in these embodiments without departing from the principles and spirit of the invention, the scope of which is defined in the accompanying claims.

What is claimed is:

1. A detected sour odor composition from an air conditioner consisting of:
    0.1-2 ppm of ammonia;
    0.002-0.1 ppm of acetaldehyde;
    0.0001-0.1 ppm of propionaldehyde;
    0.0003-0.03 ppm of n-butyraldehyde;
    0.03-30 ppm of toluene;
    0.001-2 ppm of xylene; and
    0.003-7 ppm of methyl ethyl ketone.

2. A method for analyzing compounds contributing to a sour odor from an air conditioner, comprising:
    collecting a gas emitted from an air conditioner; and
    analyzing components of the gas,
    wherein the components analyzed in the gas and that contribute to sour odor consist of: 0.1-2 ppm of ammonia; 0.002-0.1 ppm of acetaldehyde; 0.0001-0.1 ppm of propionaldehyde; 0.0003-0.03 ppm of n-butyraldehyde; 0.03-30 ppm of toluene; 0.001-2 ppm of xylene; and 0.003-7 ppm of methyl ethyl ketone.

3. The method according to claim 2, wherein the air conditioner is an automobile air conditioner.

4. The method according to claim 2, wherein the analysis of the components is performed by gas chromatography/mass spectrometry, gas chromatography with atomic emission detector, gas chromatography/flame ionization detection/olfactometry or high-performance liquid chromatography.

5. A method for preparing a detected sour odor composition from an air conditioner, comprising: mixing compounds consisting of: ammonia, acetaldehyde, propionaldehyde, n-butyraldehyde, toluene, xylene and methyl ethyl ketone.

6. The method of claim 5, wherein the detected sour odor composition from the air conditioner consists of:
    0.1-2 ppm of ammonia;
    0.002-0.1 ppm of acetaldehyde;
    0.0001-0.1 ppm of propionaldehyde;
    0.0003-0.03 ppm of n-butyraldehyde;
    0.03-30 ppm of toluene;
    0.001-2 ppm of xylene; and
    0.003-7 ppm of methyl ethyl ketone.

7. A composition for reproducing sour odor from an air conditioner consisting of:
    0.1-2 ppm of ammonia;
    0.002-0.1 ppm of acetaldehyde;
    0.0001-0.1 ppm of propionaldehyde;
    0.0003-0.03 ppm of n-butyraldehyde;
    0.03-30 ppm of toluene;
    0.001-2 ppm of xylene; and
    0.003-7 ppm of methyl ethyl ketone.

* * * * *